(12) United States Patent
Engers et al.

(10) Patent No.: US 9,211,290 B2
(45) Date of Patent: Dec. 15, 2015

(54) SOLID DISPERSIONS OF AMORPHOUS PAROXETINE MESYLATE

(71) Applicant: NOVEN THERAPEUTICS, LLC, Miami, FL (US)

(72) Inventors: David A. Engers, West Lafayette, IN (US); Yonglai Yang, West Lafayette, IN (US); Stephan Parent, West Lafayette, IN (US); Travis Houston, West Lafayette, IN (US); Bruce Charles Friedman, New York, NY (US)

(73) Assignee: NOVEN THERAPEUTICS, LLC, Miami, FL (US)

( * ) Notice: Subject to any disclaimer, the term of this patent is extended or adjusted under 35 U.S.C. 154(b) by 245 days.

(21) Appl. No.: 13/833,963

(22) Filed: Mar. 15, 2013

(65) Prior Publication Data

US 2014/0187582 A1    Jul. 3, 2014

Related U.S. Application Data

(60) Provisional application No. 61/747,387, filed on Dec. 31, 2012.

(51) Int. Cl.
| | | |
|---|---|---|
| *A61K 31/4525* | (2006.01) | |
| *A61K 9/16* | (2006.01) | |
| *A61K 9/48* | (2006.01) | |
| *A61K 9/19* | (2006.01) | |

(52) U.S. Cl.
CPC .......... *A61K 31/4525* (2013.01); *A61K 9/1635* (2013.01); *A61K 9/4866* (2013.01); *A61K 9/19* (2013.01)

(58) Field of Classification Search
CPC ... A61K 31/4525; A61K 9/1635; A61K 9/19; A61K 9/4866
See application file for complete search history.

(56) References Cited

U.S. PATENT DOCUMENTS

| 5,955,475 A | * | 9/1999 | Krape et al. | 514/321 |
| 2004/0086559 A1 | * | 5/2004 | Peters et al. | 424/465 |
| 2006/0058358 A1 | * | 3/2006 | Dumas et al. | 514/350 |
| 2008/0051427 A1 | * | 2/2008 | Schuckler | 514/292 |

* cited by examiner

*Primary Examiner* — Sreeni Padmanabhan
*Assistant Examiner* — Jody Karol
(74) *Attorney, Agent, or Firm* — Foley & Lardner LLP

(57) ABSTRACT

The invention relates to solid dispersions containing paroxetine mesylate. One solid dispersion contains amorphous paroxetine mesylate and a methacrylic acid-methyl methacrylate copolymer, where the weight ratio of paroxetine mesylate to polymer ranges from about 30:70 to about 90:10. Another solid dispersion contains amorphous paroxetine mesylate and a -vinylpyrrolidone/vinylacetate copolymer (PVP-VA), where the weight ratio of paroxetine mesylate to copolymer ranges from about 30:70 to about 50:50. An amorphous solid dispersion of the invention may have a single glass transition temperature. An amorphous solid dispersion is stable for at least 48 hours at 60° C. and 75% relative humidity. A further embodiment of the invention relates to pharmaceutical compositions of paroxetine mesylate comprising a solid dispersion of the invention and at least one pharmaceutically acceptable excipient. Methods for the treatment using paroxetine mesylate in the form of a solid dispersion according to the invention are also disclosed.

6 Claims, 16 Drawing Sheets

(top to bottom):
30/70 (w/w) PM/Eudragit L100
70/30 (w/w) PM/Eudragit L100
50/50 (w/w) PM/PVP VA
magnesium stearate
dibasic calcium phosphate (top to bottom):
as prepared
RT/58% RH/2 weeks
RT/58% RH/4 weeks
60 °C/75% RH/2 weeks
60 °C/75% RH/4 weeks
magnesium stearate
dibasic calcium phosphate.

(top to bottom):
as prepared
RT/58% RH/2 weeks
RT/58% RH/4 weeks
60 °C/75% RH/2 weeks
60 °C/75% RH/4 weeks
magnesium stearate
dibasic calcium phosphate (top to bottom):
as prepared
RT/58% RH/2 weeks
RT/58% RH/4 weeks
60 °C/75% RH/2 weeks
60 °C/75% RH/4 weeks
magnesium stearate
dibasic calcium phosphate

SOLID DISPERSIONS OF AMORPHOUS PAROXETINE MESYLATE

CROSS-REFERENCE TO RELATED APPLICATIONS

This application claims priority to U.S. application Ser. No. 61/747,387, filed Dec. 31, 2012, which is incorporated herein by reference.

FIELD OF THE INVENTION

This invention relates to solid dispersions of amorphous paroxetine mesylate. The invention also relates to pharmaceutical compositions containing the solid dispersions and to methods of treatment using them.

BACKGROUND

Paroxetine, (−)-(3S,4R)-4-(p-Fluorophenyl)-3-[[3,4-(methylenedioxy)phenoxy]methyl]piperidine, is an therapeutic agent of the type known as selective serotonin reuptake inhibitors. Paroxetine is a well characterized molecule in the pharmaceutical and patent literature. Chemical processes for its manufacture are detailed in U.S. Pat. Nos. 4,861,893; 6,172,233; 6,326,496; 6,433,179; 6,541,637 6,686,473; 6,716,985; 6,881,845; 6,900,327; and U.S. Pat. No. 6,956, 121 to name a few. Paroxetine has also been indicated for a wide range of treatments but is primarily prescribed to treat depression, obsessive compulsive disorder, post-traumatic stress disorder, panic disorder, generalized anxiety disorder, social phobia and social anxiety disorders, and premenstrual dysphoric disorder. Common off-label uses of paroxetine include the treatment of premature ejaculation, compulsive gambling, hot flashes, diabetic neuropathy, and tension headache. Paroxetine is also sometimes used to treat chronic headaches, tingling in the hands and feet caused by diabetes, and certain male sexual problems. In addition to its use for psychiatric diseases and disorders, and psychological diseases and disorders, studies have also been conducted suggesting that paroxetine is beneficial for use in the treatment, alleviation and prevention of thermoregulatory dysfunctions and vasomotor symptoms including hot flashes and hot flushes, and potentially further for, night awakenings, night sweats, and other disorders and conditions associated with perimenopause, menopause and hormonal deficiencies.

The compound has been known both in its basic form and in the form of its pharmaceutically acceptable salts since at least 1977 with the publication of U.S. Pat. No. 4,007,196. The '196 patent makes explicit reference to the paroxetine base and to its maleate salt. Paroxetine is currently marketed in the US in the form of acidic salt, the hydrochloride salt, under the trade name PAXIL and as the mesylate salt under the PEXEVA trade name.

Paroxetine hydrochloride can be crystallized in either an anhydrate or a hemihydrate crystal form: the anhydrous form in several crystalline modifications (PCT Application WO 96/24595); the hydrated form—a hemihydrate (EP patent 223403) and in the solvated forms. The comparison of behavior between the anhydrous and hydrated form of paroxetine hydrochloride is described in the Intl. Journal of Pharmaceutics, 42, 135-143 (1988). EP Patent 223403 discloses paroxetine hydrochloride hemihydrate and pharmaceutical compositions based thereon.

Many of the known salts of paroxetine have unsuitable physico-chemical characteristics for ensuring safe and efficient handling during production thereof and formulation into final forms, since they are unstable (acetate, maleate) and possess undesirable hygroscopicity. Furthermore their formation by crystallization from both aqueous and non-aqueous solvents is generally low-yielding and troublesome as they usually contain an undefined and unpredictable amount of bound solvent which is difficult to remove. The crystalline paroxetine hydrochloride hemihydrate approaches these problems, but as stated in PCT Application WO 95/16448, its limited photostability causes undesired coloration during classical wet granulation procedures. Moreover, crystalline paroxetine hydrochloride hemihydrate exhibits only limited solubility in water.

Sulfonic acid salts of paroxetine, and their crystalline form, are described in U.S. Pat. Nos. 5,874,447 and 7,509,271. The '447 patent describes paroxetine sulfonate salts, including paroxetine methane sulfonate also known as paroxetine mesylate. These sulfonate salts have advantageous properties in comparison to the known salts, including the hydrochloride salts. For example, the sulfonate salts have high water solubility and good thermal stability, making them useful as a commercial paroxetine dosage form. The '447 patent discloses that tablets can be made by any known method including a dry technique (direct compression, dry granulation) or a wet technique (wet granulation). Example 1 of those patents describe the preparation of paroxetine mesylate, also known as the methane sulfonic acid salt of paroxetine, and shown in structural formula (I) below.

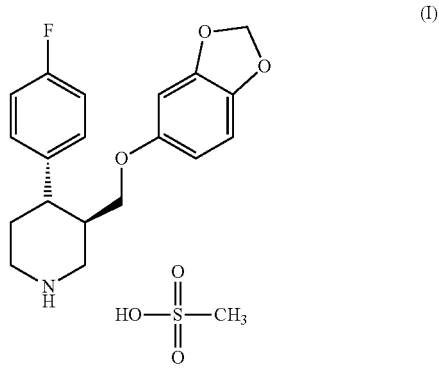

(I)

U.S. Pat. No. 6,063,927 "generally" refers to the ability to make the mesylate salt in a non-crystalline form (solid or an oil), and in solvated forms, but provides no specifics other than creating an acetonitrile solvated form, which is unsuitable for commercial application, and an amorphous form. U.S. Pat. No. 7,509,271 describes the only crystalline form of paroxetine mesylate, an anhydrous crystalline form designated Form A). Paroxetine mesylate has no known polymorphs.

The amorphous form of a drug may temporarily provide a greater aqueous concentration of drug relative to the equilibrium concentration obtained by dissolution of the crystalline drug in a use environment. Such amorphous forms may consist as the amorphous drug alone, a solid dispersion of the amorphous drug in a matrix material, or the amorphous drug adsorbed onto a substrate. It is believed that such amorphous forms of the drug may dissolve more rapidly than the crystalline form, often dissolving faster than the drug can precipitate from solution. As a result, the amorphous form may temporarily provide a greater aqueous concentration of drug.

While such amorphous forms may show initially enhanced concentration of the drug in a use environment, nevertheless the improved concentration may often be short-lived. The initially enhanced drug concentration may be only temporary and quickly return to the lower equilibrium concentration of a crystalline form. Amorphous paroxetine mesylate may be generated through lyophilization from water having a glass transition temperature of approximately 44° C.; but it is physically unstable and over time converts to crystalline Form A. Various amorphous paroxetine compositions have been disclosed, for example, in U.S. Pat. Nos. 5,672,612, 6,503,927, 6,638,948, 6,169,805, 6,720,003, and 6,063,927.

As mentioned above, one approach to increasing the stability of amorphous drug forms involves forming dispersions of amorphous drugs with polymers. Use of amorphous compositions for advanced drug delivery systems includes oral capsules, an example of which is an amorphous paroxetine composition disclosed in PCT Application WO 99/16440. PCT Application WO 99/56751 describes amorphous paroxetine formulations which are produced by mixing paroxetine salts, preferably the hydrochloride, with water and a polymer and subsequently drying at 25 -100° C., preferably at 60° C. PCT Application WO 01/30349 likewise relates to the processing of amorphous paroxetine salts in polyvinylpyrrolidone and an additional acid. Production takes place at temperatures of 15-40° C. Other examples of attempts to form a dispersion of the drug with a polymer include U.S. Pat. Nos. 5,368,864, 5,707,655, and 5,456,923, and EP publication 0901786A2.

One problem with trying to use the pure amorphous form of a drug in a drug delivery dosage form is that the solid drug may not be stable physically in the amorphous form. Often the crystalline form of the drug has a lower free energy such that, over time, the amorphous drug will tend to crystallize. This has been observed with the amorphous form of paroxetine mesylate which converts to crystalline paroxetine mesylate, Form A. The rate of crystallization may be influenced by storage conditions, such as temperature and humidity, as well as the constituents of the composition.

Similarly, even if a dispersion of drug and polymer is formed, the drug in the resulting amorphous dispersion of polymer and drug may in some cases be unstable. For example, the dispersion may be physically unstable over time at moderate temperatures and humidities, causing the amorphous drug to separate from the dispersion and/or crystallize. Alternatively, the drug in the amorphous dispersion may be chemically unstable.

Alternatively, it may be difficult or, in some cases, impossible to form a dispersion of the drug and preferred polymer. In particular, the drug and preferred polymer may not both be amenable to a processing method that results in a dispersion of the drug and preferred polymer. For example, when solvent processing is the preferred method for forming the dispersion, the drug and preferred polymer may not both be soluble to a sufficient extent in an appropriate processing solvent to allow formation of the dispersion. In cases where melt processing is preferred, the drug or polymer or both may suffer unacceptable decomposition upon heating to allow the formation of the preferred composition to be practical.

Accordingly, for paroxetine mesylate what would be desirous is a composition comprising that amorphous drug that is physically and/or chemically stable under typical storage conditions, that may be formed via practical processing conditions, and/or that may enhance the bioavailability of paroxetine mesylate. These needs and others that will become apparent to one of ordinary skill are met by the invention, which is summarized and described in detail below.

SUMMARY OF THE INVENTION

The invention relates to solid dispersions containing amorphous paroxetine mesylate. One solid dispersion of the invention contains amorphous paroxetine mesylate and a methacrylic acid-methyl methacrylate copolymer, where the weight ratio of paroxetine mesylate to polymer ranges from about 30:70 to about 90:10. Another solid dispersion of the invention contains amorphous paroxetine mesylate and a copolymer of vinylpyrrolidone and vinyl acetate (PVP-VA), where the weight ratio of paroxetine mesylate to copolymer ranges from about 30:70 to about 50:50. An amorphous solid dispersion of the invention may have a single glass transition temperature. In another embodiment an amorphous solid dispersion is stable for at least 48 hours at 60° C. and 75% relative humidity.

A further embodiment of the invention relates to pharmaceutical compositions of paroxetine mesylate comprising a solid dispersion of the invention and at least one pharmaceutically acceptable excipient. The paroxetine mesylate is present in the pharmaceutical composition in a therapeutically acceptable amount.

The invention also provides for the treatment of thermoregulatory dysfunction and in particular to such conditions (without limitation) as hot flushes, hot flashes, night sweats, etc. whether or not related to menopause (female or male), perimenopause, hormone ablative therapy (including, but not limited to, anti-estrogenic therapy and antiandrogenic therapy), treatments with other chemical agent or therapeutic agents that are antiestrogenic or antiandrogenic or interfere with thermoregulatory function, surgical procedures (such as, without limitation castration, hysterectomy, ooectomy, etc), and disease states interfering with normal thermoregulatory functioning, by administration of a therapeutically effective amount of paroxetine mesylate in the form of a solid dispersion of the invention. Most preferably, the present invention is directed to the treatment of perimenopausal and postmenopausal hot flashes, hot flushes and night sweats in women, whether due to aging, therapeutically induced menopause, or surgically induced menopause. The invention is also preferably directed to hot flashes or hot flushes or night sweats in men whether such symptoms are due to aging, chemical castration, hormonal ablative therapy, or surgical castration.

DETAILED DESCRIPTION

Figure 1:
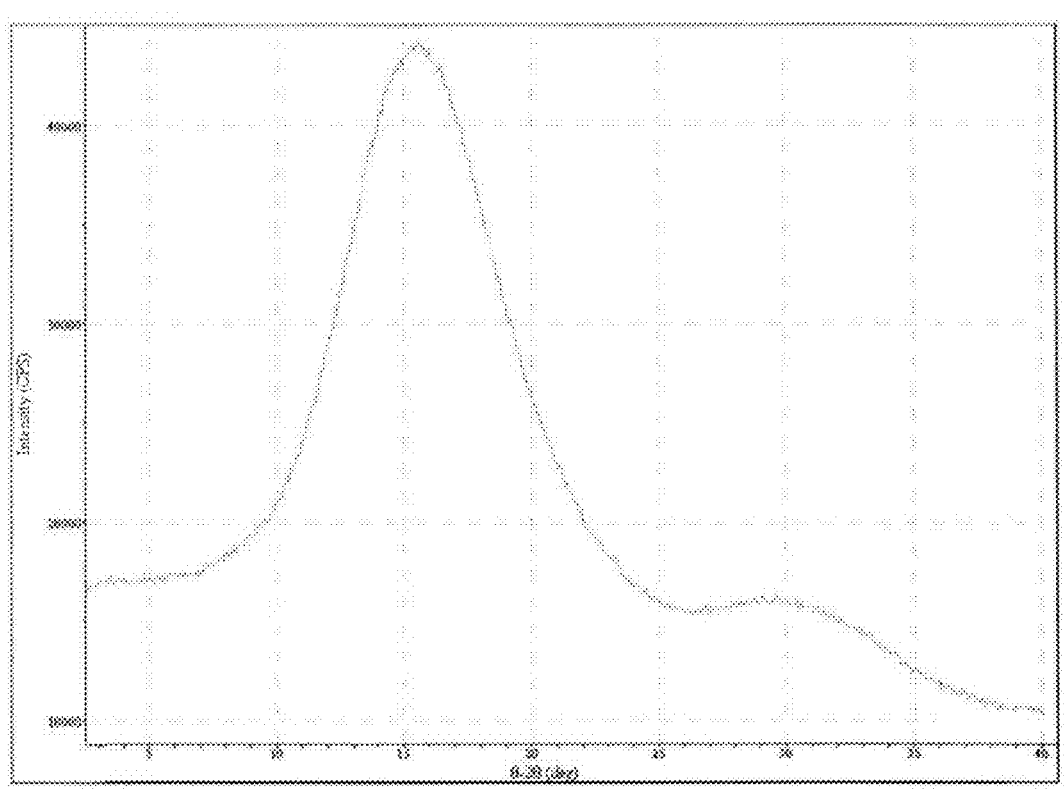
FIG. 1 depicts the XRPD pattern of a 30/70 (w/w) amorphous paroxetine mesylate/Eudragit L100 solid dispersion, Example 2-1, prepared by spray drying.

The invention relates to solid dispersions of amorphous paroxetine mesylate in a methacrylic acid-methyl methacrylate copolymer or in a polyvinylpyrrolidone vinyl acetate (PVP-VA) copolymer. The amorphous nature of the solid dispersions is determined by X-ray powder diffraction (XRPD). A material is "X-ray amorphous" when there are no sharp peaks observed in its XRPD pattern, only broad halos. Sharp peaks in the XRPD indicate the presence of crystalline material. B. D. Cullity & S. R. Stock, Elements of X-Ray Diffraction, 3rd Ed., Prentice-Hall Inc., 2001, p 182-183, ISBN 0-201-61091-4; and S. Bates, G. Zografi, D. A. Engers, K. R. Morris, K. Crowley, and A. W. Newman, "Analysis of Amorphous and Nanocrystalline Solids from Their X-Ray Diffraction Patterns" Pharm Res 23(10): 2333-2349 (2006). The solid dispersions of the invention are "X-ray amorphous" as their XRPD patterns do not exhibit sharp peaks, only broad halos.

An amorphous solid dispersion of the invention may also be characterized by a single glass transition temperature ($T_g$). Displaying a single glass transition temperature is classically taken to indicate that the components of the amorphous solid dispersion are miscible. Two or more glass transition temperatures indicates that more than one of the components used are amorphous and immiscible or phase separate. The $T_g$ of an amorphous solid dispersion is typically measured by differential scanning calorimetry (DSC). The measured glass transition temperatures of exemplary amorphous solid dispersions according to the invention are reported below in the Examples.

The amorphous solid dispersions of the invention are also physically stable. Amorphous solid dispersions of the invention exhibit high physical stability for long periods of time at various temperatures and at various humidity levels. In different embodiments, an amorphous solid dispersion of the invention may be physically stable at room temperature (RT, e.g. about 25° C.) and 58% relative humidity (RH) for at least 3 days, or a 60° C. and 75% RH for at least 2 hours, for at least 20 hours, for at least 48 hours, for at least 6 days, or even for at least 14 days. The polymer in an amorphous solid dispersion of the invention stabilizes the amorphous paroxetine mesylate so as to prevent crystallization, e.g, the formation of crystalline paroxetine mesylate, Form A, as discussed above. The polymer also provides physical stability over time and under a variety of environmental conditions, such as elevated temperature and relative humidity (RH). The physical stability of the amorphous solid dispersions of the invention is shown by the absence of crystalline materials when subjected to one or more of the temperature and humidity conditions discussed. In one embodiment, an amorphous solid dispersion of the invention is stable for at least 48 hours at 60° C. and 75% relative humidity.

In one embodiment, the invention relates to a solid dispersion of amorphous paroxetine mesylate in a methacrylic acid-methyl methacrylate copolymer. The methacrylic acid-methyl methacrylate copolymer is an anionic copolymer. One suitable methacrylic acid-methyl methacrylate copolymer is sold by Evonik Industries under the Eudragit® L100 tradename. The Eudragit® L100 copolymer is an anionic 1:1 methacrylic acid-methyl methacrylate copolymer, CAS number 25086-15-1, which dissolves in water above pH 6, has a weight average molecular mass of approximately 125,000 g/mol, an acid value of 315 mg KOH/g polymer and a glass transition temperature ($T_g$) of 150° C.

When an amorphous solid dispersion of the invention contains a methacrylic acid-methacrylate copolymer, the weight ratio of paroxetine mesylate to polymer ranges from about 30:70 to about 90:10. In exemplary embodiments of such a solid dispersion the weight ratio is selected from about 30:70, about 70:30 and about 90:10.

In one embodiment, the invention relates to a solid dispersion of amorphous paroxetine mesylate in a polyvinylpyrrolidone-vinyl acetate (PVP-VA) copolymer. The PVP-VA is supplied by Aldrich, is a 1.3:1 PVP-VA copolymer, CAS number 25086-89-9, which has a weight average molecular mass of approximately 50,000 g/mol and a glass transition temperature ($T_g$) of 64° C.

When a solid dispersion of the invention contains a PVP-VA copolymer, the weight ratio of paroxetine mesylate to polymer ranges from about 30:70 to about 50:50. In exemplary embodiments of such a solid dispersion the weight ratio is selected from about 30:70 and about 50:50.

Methods of Making a Solid Dispersion of the Invention

A solid dispersion containing amorphous paroxetine mesylate according to the invention may be prepared using known techniques such as spray-drying (SD) or freeze drying (FD). Spray drying is a preferred technique to prepare an amorphous sold dispersion of the invention and may be used for small scale and commercial scale production. In an embodiment of the invention, a solution of paroxetine mesylate and the copolymer are dissolved in a suitable solvent to form a solution and then spray dried or freeze dried to form an amorphous solid dispersion. Such methods are known in the art and described in the examples below.

Pharmaceutical Compositions and Methods of Treatment

A solid dispersion of the invention may be used in the same way as other known therapeutic compositions containing paroxetine or a paroxetine salt to deliver a therapeutically effective amount of paroxetine mesylate. For the treatment of thermoregulatory dysfunction and in particular to such conditions (without limitation) as hot flushes, hot flashes, night sweats, etc. whether or not related to menopause (female or male), perimenopause, hormone ablative therapy (including, but not limited to, anti-estrogenic therapy and antiandrogenic therapy), treatments with other chemical agent or therapeutic agents that are antiestrogenic or antiandrogenic or interfere with thermoregulatory function, surgical procedures (such as, without limitation castration, hysterectomy, ooectomy, etc), and disease states interfering with normal thermoregulatory functioning, by administration of a therapeutically effective amount of paroxetine mesylate in the form of an amorphous solid dispersion, the dosage is about 0.1 mg/day up to less than an antidepressant effective amount of paroxetine (based on the active moiety); preferably up to about 19.5 mg/day. Preferably the paroxetine can be administered to achieve the invention in amounts of at least 5 mg/day, more preferably at least 7.5 mg/day, up to preferably not more than about 15 mg/day. Other non-limiting dosages that are specifically suitable for the present invention include 2 mg/day, 2.5 mg/day, 3 mg/day, 3.5 mg/day, 4 mg/day, 4.5 mg/day, 5 mg/day, 5.5 mg/day, 6 mg/day, 6.5 mg/day, 7 mg/day, 7.5 mg/day, 8 mg/day, and 8.5 mg/day. In general, the recommended starting dose of paroxetine for depression is 20 mg/day. Elderly people and those with kidney or liver problems may be started on a lower dose of the medication. Paroxetine dosing for people with panic disorder usually starts at 10 mg/day. The maximum paroxetine dosage is usually 50 mg or 60 mg/day, depending on the condition being treated.

Most preferably, an embodiment of the invention relates to a pharmaceutical composition of paroxetine mesylate comprising a solid dispersion of the invention and at least one pharmaceutically acceptable excipient. The paroxetine mesylate is present in the pharmaceutical composition in a therapeutically acceptable amount. Another embodiment of the invention relates to a method for the treatment of depression comprising the step of administering to a patient in need thereof a therapeutically effective amount of paroxetine mesylate in the form of a solid dispersion of the invention. As is known in the art, the pharmaceutically acceptable excipients may be utilized in order to formulate the composition into tablets, capsules, suppositories, suspensions, powders for suspension, creams, transdermal patches, depots, and the like. A pharmaceutical composition of the invention may be made by techniques know in the art. The mixture may be added to other dosage form ingredients in essentially any manner that does not substantially alter the drug. The excipients may be either separate from the mixture and/or included within the mixture. The addition of pH modifiers such as acids, bases, or buffers may be beneficial, retarding the dissolution of the composition (e.g., acids such as citric acid or succinic acid when the concentration-enhancing polymer is anionic) or, alternatively, enhancing the rate of dissolution of the composition (e.g., bases such as sodium acetate or amines when the polymer is anionic).

Conventional matrix materials, complexing agents, solubilizers, fillers, disintegrating agents (disintegrants), or binders may also be added as part of the composition itself or added by granulation via wet or mechanical or other means. These materials may comprise up to 90 wt % of the composition. Examples of matrix materials, fillers, or diluents include lactose, mannitol, xylitol, microcrystalline cellulose, dibasic calcium phosphate (dihydrate and anhydrous), and starch. Examples of disintegrants include sodium starch glycolate, sodium alginate, carboxy methyl cellulose sodium, methyl cellulose, and croscarmellose sodium, and crosslinked forms of polyvinyl pyrrolidone such as those sold under the trade name CROSPOVIDONE (available from BASF Corporation). Examples of binders include methyl cellulose, microcrystalline cellulose, starch, and gums such as guar gum, and tragacanth. Examples of lubricants include magnesium stearate, calcium stearate, and stearic acid. Examples of preservatives include sulfites (an antioxidant), benzalkonium chloride, methyl paraben, propyl paraben, benzyl alcohol and sodium benzoate. Examples of suspending agents or thickeners include xanthan gum, starch, guar gum, sodium alginate, carboxymethyl cellulose, sodium carboxymethyl cellulose, methyl cellulose, hydroxypropyl methyl cellulose, polyacrylic acid, silica gel, aluminum silicate, magnesium silicate, and titanium dioxide. Examples of anticaking agents or fillers include silicon oxide and lactose. Examples of solubilizers include ethanol, propylene glycol or polyethylene glycol.

Other conventional excipients may be employed in the compositions of this invention, including those excipients well-known in the art. Generally, excipients such as pigments, lubricants, flavorants, and so forth may be used for customary purposes and in typical amounts without adversely affecting the properties of the compositions. These excipients may be utilized in order to formulate the composition into tablets, capsules, suspensions, powders for suspension, creams, transdermal patches, and the like.

EXAMPLES

Solid dispersions of the invention containing amorphous paroxetine mesylate (PM) were prepared using two polymers: Eudragit L100 and poly(1-vinylpyrrolidone-co-vinyl acetate) (PVP-VA). Both polymers are non-crystalline and thus the solid dispersions are themselves amorphous. The solid dispersions were characterized and tested as described below.

Instrumental Techniques

Modulated Differential Scanning calorimetry (mDSC): MDSC data were obtained on a TA Instruments differential scanning calorimeter Q2000 equipped with a refrigerated cooling system (RCS). The sample was placed into an aluminum DSC pan, and the weight accurately recorded. The pan was covered with a lid and then crimped. MDSC data were obtained using a modulation amplitude of +/−0.5° C. and a 60 second period with an underlying heating rate of 2° C./min. The temperature and the heat capacity were calibrated using indium metal and sapphire as the calibration standards, respectively. The reported $T_g$ is obtained from the half-height/inflection of the step change in the reversible heat flow versus temperature curve.

X-ray Powder Diffraction (XRPD): XRPD patterns were collected using a PANalytical X'Pert Pro diffractometer. The specimen was analyzed using Cu radiation produced using an Optix long fine-focus source. An elliptically graded multilayer mirror was used to focus the Cu Kα X-rays of the source through the specimen and onto the detector. The specimen was sandwiched between 3-micron thick films, analyzed in transmission geometry, and rotated to optimize orientation statistics. Soller slits were used for the incident and diffracted beams to minimize axial divergence. Diffraction patterns were collected using a scanning position-sensitive detector (X'Celerator) located 240 mm from the specimen. Prior to the analysis, a silicon specimen (NIST standard reference material 640d) was analyzed to verify the position of the silicon 111 peak.

Polarized Light Microscopy (PLM): Polarized light microscopy was performed using a Leica DM LP microscope equipped with Spot Insight color camera (model 3.2.0). Samples were placed onto glass slides or left in vial and observed using a Leica MZ12.5 stereomicroscope with crossed-polarized light and a first order red compensator.

Images were acquired at ambient temperature using Spot software (v.4.5.9 for Windows).

Scanning Electron Microscopy (SEM): SEM was performed using a FEI Quanta 200 scanning electron microscope. Under high vacuum mode, an Everhart Thornley (ETD) detector was used. Beam voltage was 5.0 kV and the resolution of the acquired image was 1024×884. Samples were sputter coated once or twice using a Cressington 108 auto Sputter Coater at ~20 mA and ~0.13 mbar (Ar) with Au/Pd for 75 seconds. Samples were prepared for analysis by placing a small amount on carbon adhesive tab fixed to an aluminum sample mount. The instrument was calibrated for magnification using NIST standards. Data were collected using xTm (v. 2.01), build number i927 and analyzed using XT Docu (v. 3.2), build 589. Magnifications reported on the SEM images were calculated upon the initial data acquisition. The scale bar reported in the lower portion of each image is accurate upon resizing the images and should be utilized when making size determinations.

Karl-Fischer (KF) Analysis: Coulometric Karl Fischer (KF) analysis for water determination was performed using a Mettler Toledo DL39 Karl Fischer titrator. Sample was placed in the KF titration vessel containing of Hydranal—Coulomat AD or AK and mixed for 10 seconds to ensure dissolution. The sample was then titrated by means of a generator electrode which produces iodine by electrochemical oxidation: $2\text{I}^- \Rightarrow \text{I}_2 + 2e$. Two replicates were obtained to ensure reproducibility.

Figure 15:
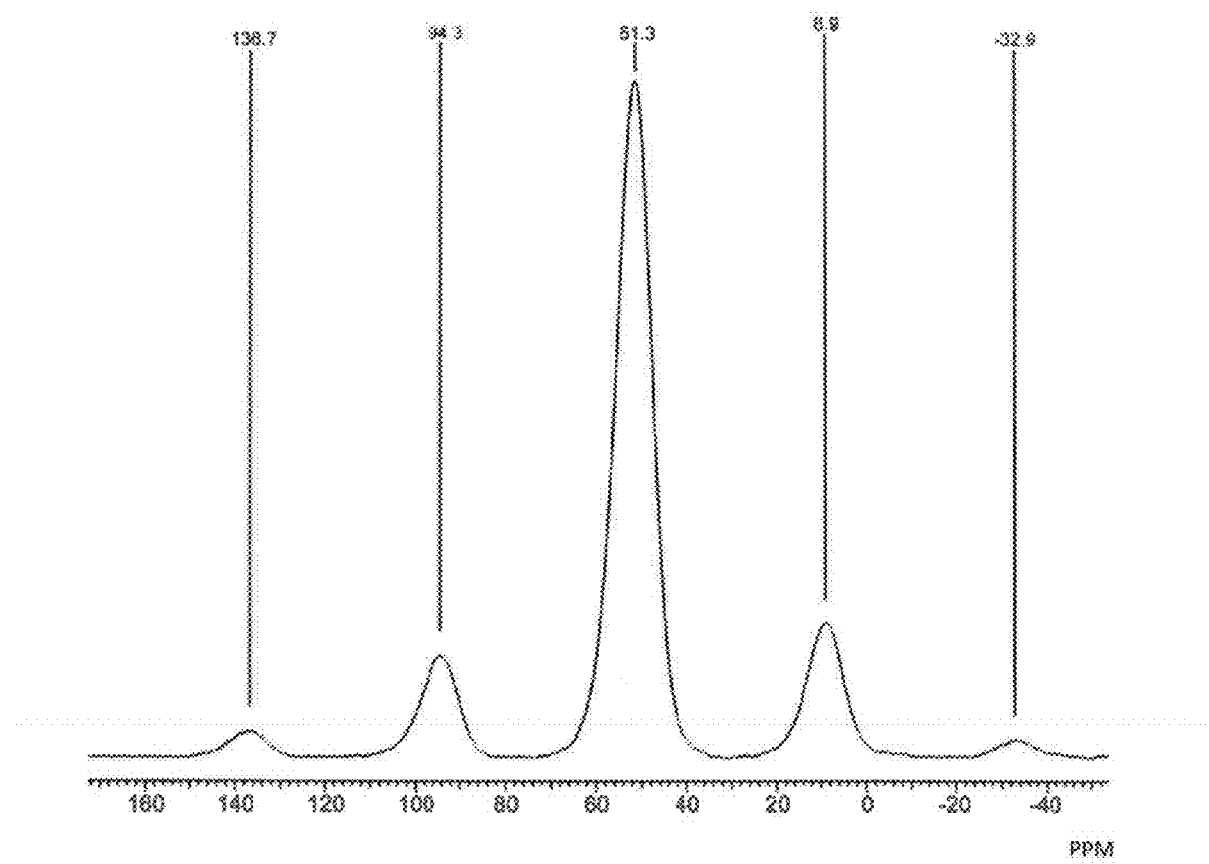
FIG. 15 is a solid state $^{19}$F SSNMR spectrum of a 30/70 (w/w) solid dispersion of amorphous paroxetine mesylate (PM) in Eudragit L100.
Figure 16:
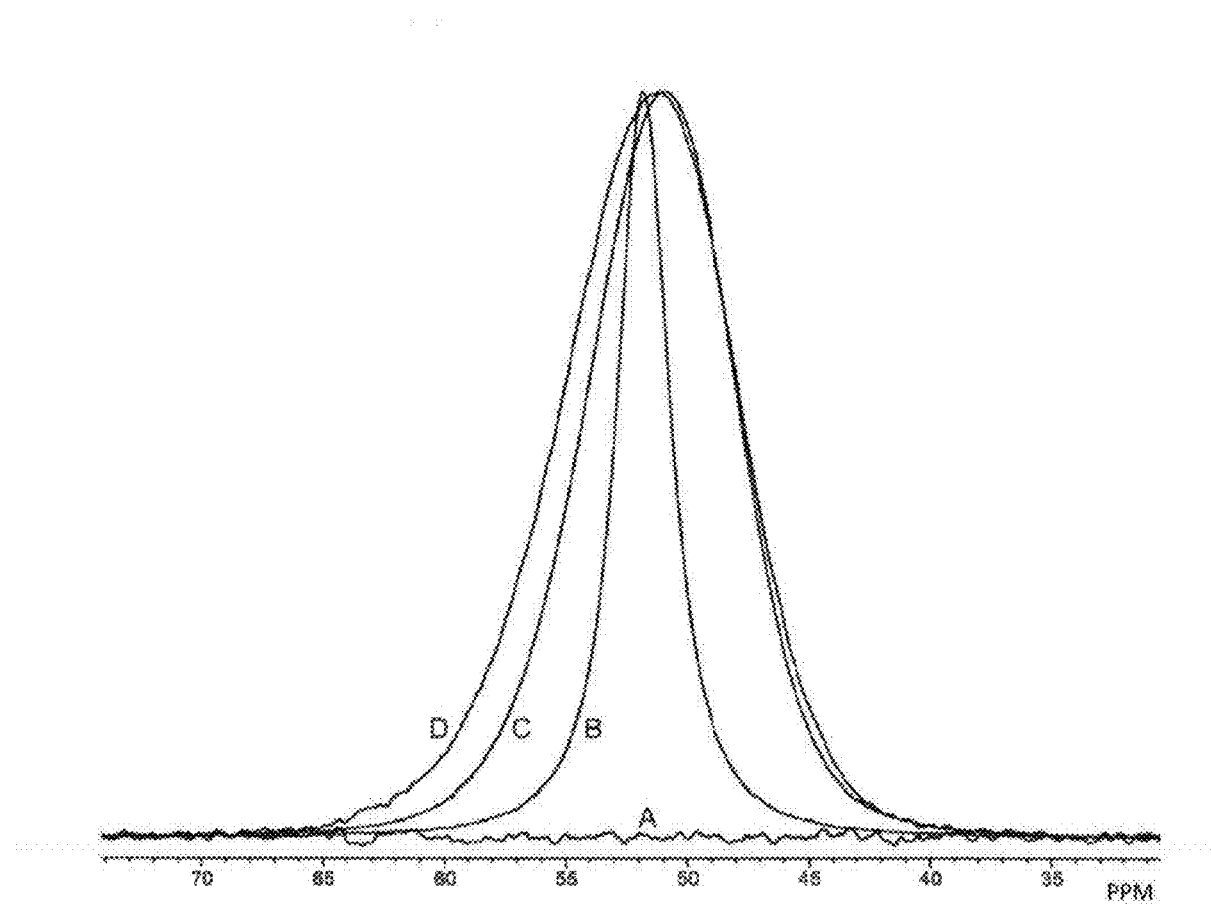
FIG. 16 is a comparison of the solid state $^{19}$F SSNMR spectra of A) spray-dried Eudragit L100; B) crystalline paroxetine mesylate Form A; C) lyophilized (amorphous) paroxetine mesylate; D) 30/70 (w/w) amorphous paroxetine mesylate/Eudragit L100 solid dispersion.

Solid State $^{19}$F NMR Analysis: Solid-state $^{19}$F NMR spectra were acquired at ambient temperature on a Varian UNITY/NOVA-400 spectrometer. The samples were packed into 4 mm PENCIL type zirconia rotors. Each free induction decay (FID) was processed using Varian VNMR 6.1C software. The first three data points of each FID were back predicted using the VNMR linear prediction algorithm to produce a flat baseline. The solid-state $^{19}$F magic angle spinning (MAS) NMR spectra were acquired at a $^{19}$F Larmor frequency of 376.134 MHz. The sample was rotated at 16 kHz at the magic angle. The spectra were acquired with a standard $^{19}$F MAS experiment without high power $^1$H decoupling using a $^{19}$F pulse width of 2.5 μs, a 30 ms acquisition time, a 20 or 30 second delay between scans, a spectral width of 100 kHz with 6000 data points, 100 co-added scans, 32768 transform points, and an exponential line broadening factor of 500 Hz (FIG. 15, peak positions) and 100 Hz (FIG. 16, comparison of peak width) to improve the signal-to-noise ratio. The chemical shifts of the spectral peaks were externally referenced to fluoroapatite at 64 ppm.

Example 1

Preparation of Solid Dispersions

Solid dispersions were prepared by freeze drying (FD) or spray drying (SD). The composition of each dispersion is expressed as the weight fraction of paroxetine mesylate (PM) versus the polymer. For example, a dispersion sample containing 70% paroxetine mesylate and 30% PVP-VA is expressed as '70/30 PM/PVP-VA'. Table 1 describes the composition of the solid dispersions made according to this example. As shown in Table 1, paroxetine mesylate itself (e.g., without a polymer) was freeze dried and spray dried for the purpose of comparison.

Freeze Drying (FD, Lyophilization): Dispersions with polymers that dissolve in water were prepared by freeze drying aqueous solutions at various paroxetine mesylate/polymer loadings in a benchtop lyophilizer. Dispersions containing PVP-VA were prepared in this manner. Multiple loadings of 70/30, 50/50, and 30/70 were generated.

Spray Drying (SD): Eudragit L100 was dissolved in methanol along with the paroxetine mesylate and spray dried on a Buchi B-290 mini spray dryer. The inlet temperature was set at 120° C. and outlet temperatures ranged from 55° C. to 79° C. Dispersions containing Eudragit L100 at a single composition of 70/30 were prepared in this manner.

Paroxetine mesylate (PM) solid dispersions were prepared as described above using the following solutions:

Example 1-1

1.6 g PM in 20 mL methanol

Example 1-2

0.50 g PM in 5 mL water

Example 1-3

1.4 g PM and 0.60 g Eudragit L100 in 40 mL methanol, 1.3 g solid was recovered

Example 1-4

2.0 g Eudragit L100 in 50 mL methanol, 1.3 g solid was recovered

Example 1-5

0.36 g PM and 0.15 g PVP-VA in 5 mL water

Example 1-6

0.25 g PM and 0.25 g PVP-VA in 5 mL water

Example 1-7

0.15 g PM and 0.35 g PVP-VA in 5 mL water; and

Example 1-8

0.17 g PVP-VA in 5 mL water

The results are shown in Table 1. Successful dispersions of amorphous paroxetine mesylate in the polymer were x-ray amorphous, as determined by XRPD analysis, and are designated as 'Amorphous'. As shown in Table 1, Eudragit L-100 itself (e.g., without paroxetine mesylate) was spray dried from methanol for the purpose of comparison.

TABLE 1

Generation of Paroxetine Mesylate (PM) Solid Dispersions

| Example | Polymer | PM wt % | Method (solvent) | Result |
|---|---|---|---|---|
| 1-1 | — | 100 | SD, methanol | Failed, no solid collected |
| 1-2 | — | 100 | FD, water | Amorphous |
| 1-3 | Eudragit L100 | 70 | SD, methanol | Amorphous |
| 1-4 | Eudragit L100 | 0 | SD, methanol | Amorphous |
| 1-5 | PVP-VA | 70 | FD, water | Amorphous |
| 1-6 | PVP-VA | 50 | FD, water | Amorphous |
| 1-7 | PVP-VA | 30 | FD, water | Amorphous |
| 1-8 | PVP-VA | 0 | FD, water | Amorphous |

Example 2

Solid Dispersions by Spray Drying

Preparation of Solid Dispersions by Spray Drying

Solid dispersions of the invention were prepared by spray drying using Büchi B-290 Mini Spray Dryer in closed mode suitable for processing organic solvents. Solutions of paroxetine mesylate (PM) and polymer were prepared in methanol as described below. Solvent only solution was first sprayed until the inlet and outlet temperatures of spray dryer were stable. Sample solution was then sprayed and the solids separated from the process gas by a glass cyclone into a glass vial. After the sample solution was sprayed, the solvent only solution was sprayed to clean the feeding tube and nozzle. The solids recovered were dried at 40° C. under vacuum for approximately 24 hours and then stored in the freezer over desiccant. Table 2 identifies the solid dispersions prepared by this method.

Example 2-1

7.5 g PM and 17.5 g Eudragit L100 in 1000 mL methanol, 15.2 g solid was recovered

Example 2-2

12.5 g PM and 12.5 g PVP-VA in 500 mL methanol, 17.3 g solid was recovered

Example 2-3

17.5 g PM and 7.5 g Eudragit L100 in 500 mL methanol, 17.6 g solid was recovered

Example 2-4

4.5 g PM and 0.50 g PVP-VA in 100 mL methanol, 2.1 g solid was recovered; and

Example 2-5

22.5 g PM and 2.5 g Eudragit L100 in 500 mL methanol, 15.3 g solid was recovered

TABLE 2

Generation of Paroxetine Mesylate Solid Dispersions by Spray Drying (SD)

| Example | PM/polymer loading, wt % | Polymer | Solvent |
| --- | --- | --- | --- |
| 2-1 | 30/70 | Eudragit L100 | Methanol |
| 2-2 | 50/50 | PVP-VA | Methanol |
| 2-3 | 70/30 | Eudragit L100 | Methanol |
| 2-4 | 90/10 | PVP-VA | Methanol |
| 2-5 | 90/10 | Eudragit L100 | Methanol |

Characterization of Spray Dried Solid Dispersions

The solid dispersions were characterized by their XRPD patterns and by the $T_g$ measured by mDSC. The results are discussed below and summarized in Table 3.

Figure 2:
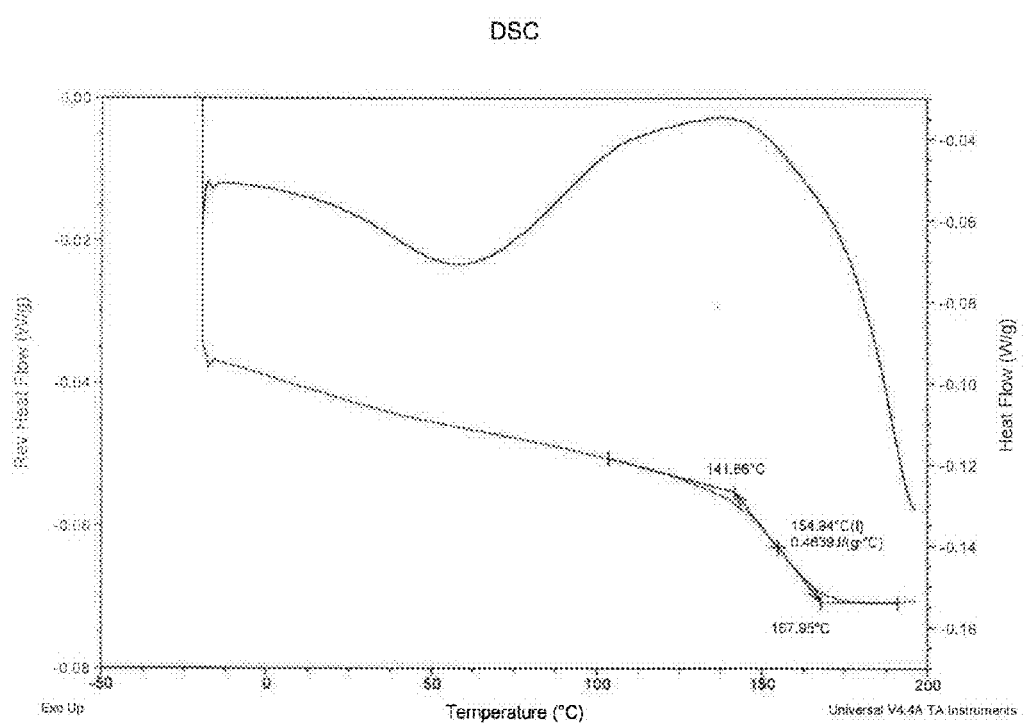
FIG. 2 depicts the modulated DSC thermogram of a 30/70 (w/w) amorphous paroxetine mesylate/Eudragit L100 solid dispersion, Example 2-1, prepared by spray drying.

XRPD pattern for 30/70 (w/w) paroxetine mesylate/Eudragit L100, Example 2-1, shows the solid dispersion to be x-ray amorphous (FIG. 1). By mDSC, a single apparent $T_g$ was observed for this sample at approximately 155° C. (FIG. 2), which is greater than the $T_g$ of amorphous paroxetine mesylate (44° C.).

Figure 3:
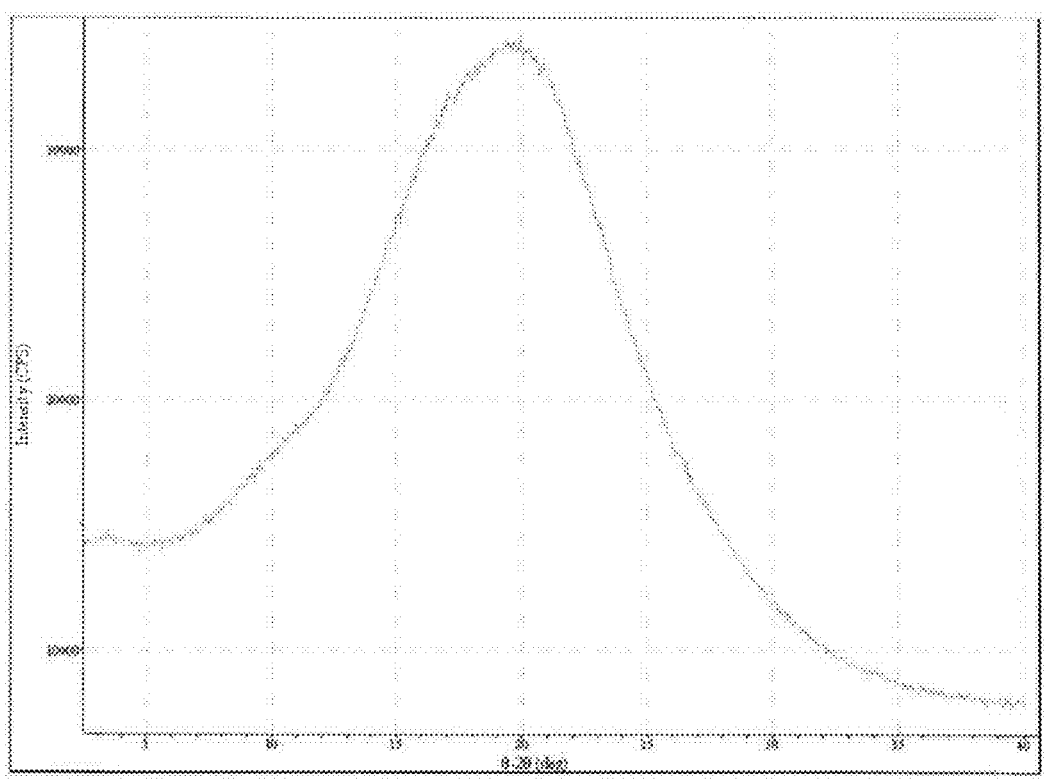
FIG. 3 depicts the XRPD pattern of a 50/50 (w/w) amorphous paroxetine mesylate/PVP-VA solid dispersion, Example 2-2, prepared by spray drying.

XRPD pattern for 50/50 (w/w) paroxetine mesylate/PVP-VA, Example 2-2, shows the solid dispersion to be x-ray amorphous (FIG. 3). By mDSC, a single apparent $T_g$ was observed for this sample at approximately 82° C. (FIG. 4), which is greater than the $T_g$ of amorphous paroxetine mesylate (44° C.).

Figure 5:
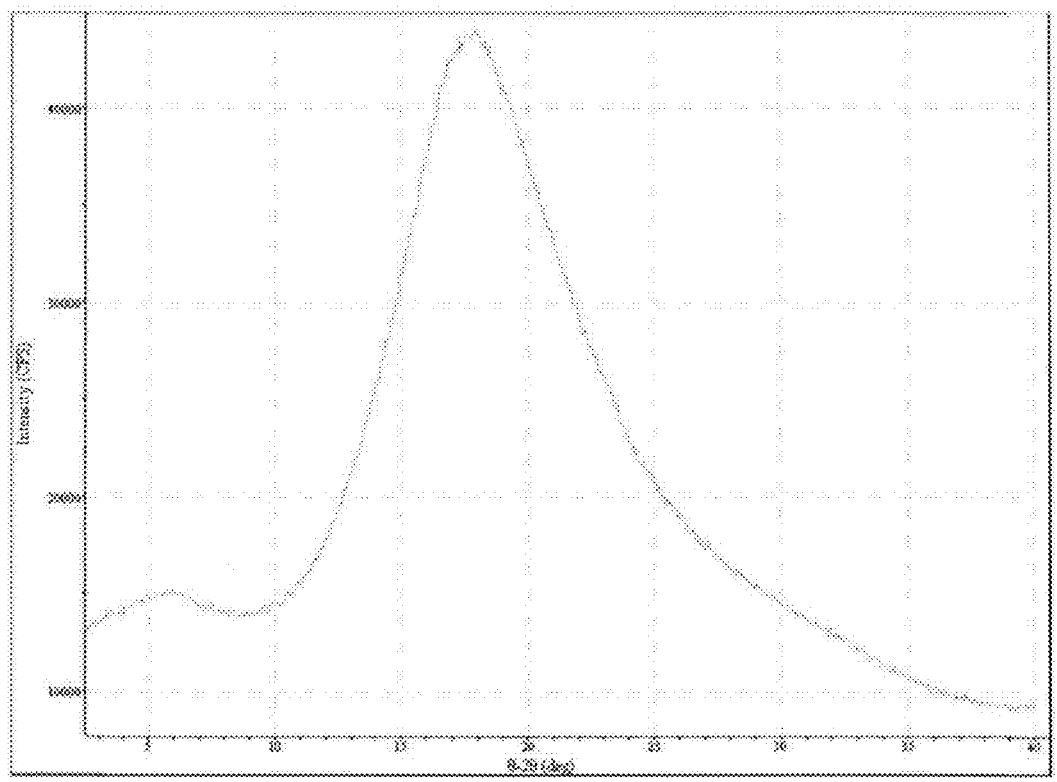
FIG. 5 depicts the XRPD pattern of a 70/30 (w/w) amorphous paroxetine mesylate/Eudragit L100 solid dispersion, Example 2-3, prepared by spray drying.
Figure 6:
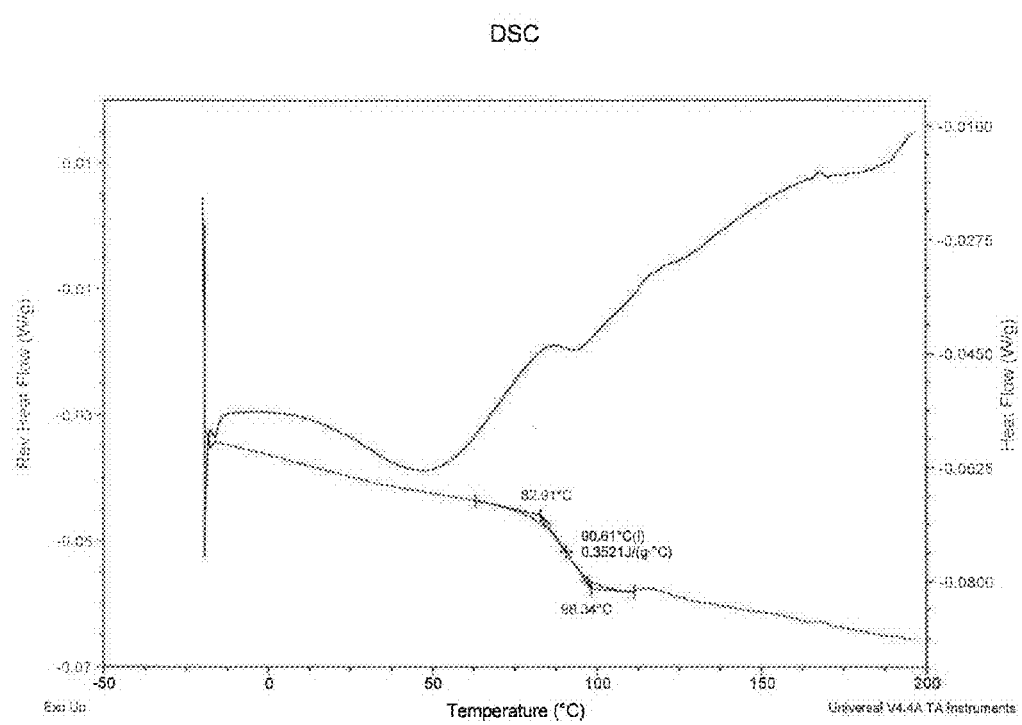
FIG. 6 depicts the modulated DSC thermogram of a 70/30 (w/w) amorphous paroxetine mesylate/Eudragit L100 solid dispersion, Example 2-3, prepared by spray drying.

XRPD pattern for 70/30 (w/w) paroxetine mesylate/Eudragit L100, Example 2-3, shows the solid dispersion to be x-ray amorphous (FIG. 5). By mDSC, a single apparent $T_g$ was observed for this sample at approximately 91° C. (FIG. 6), which is greater than the $T_g$ of amorphous paroxetine mesylate (44° C.).

Figure 7:
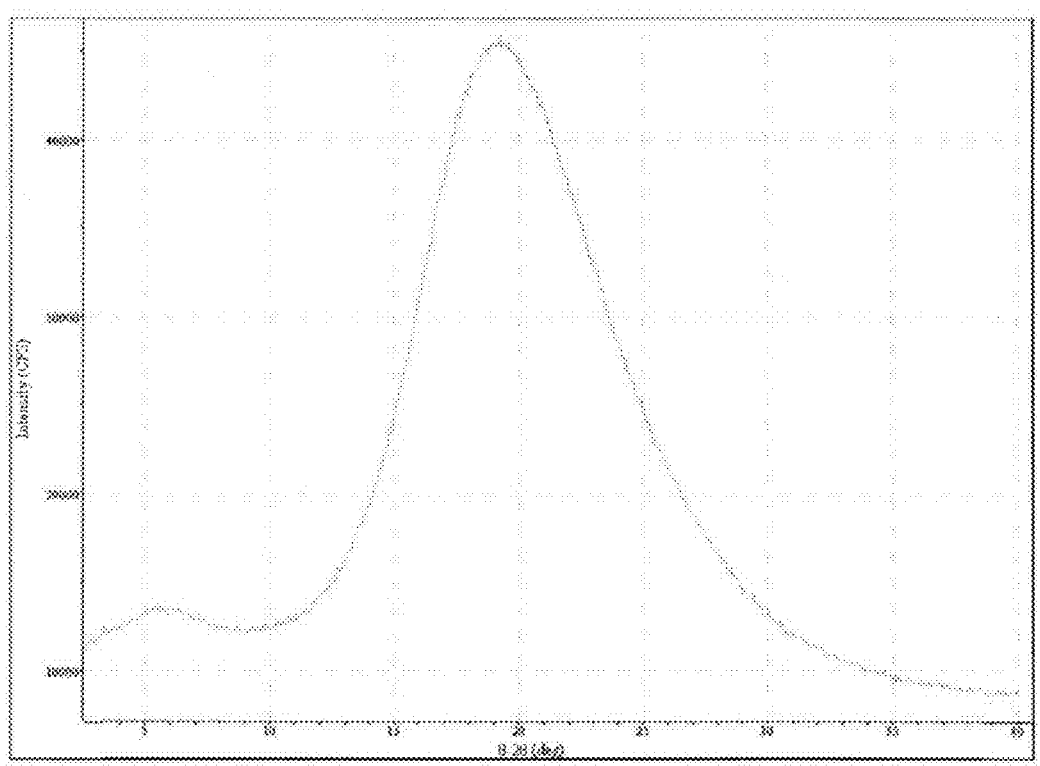
FIG. 7 depicts the XRPD pattern of a 90/10 (w/w) amorphous paroxetine mesylate/PVP-VA solid dispersion, Example 2-4, prepared by spray drying.
Figure 8:
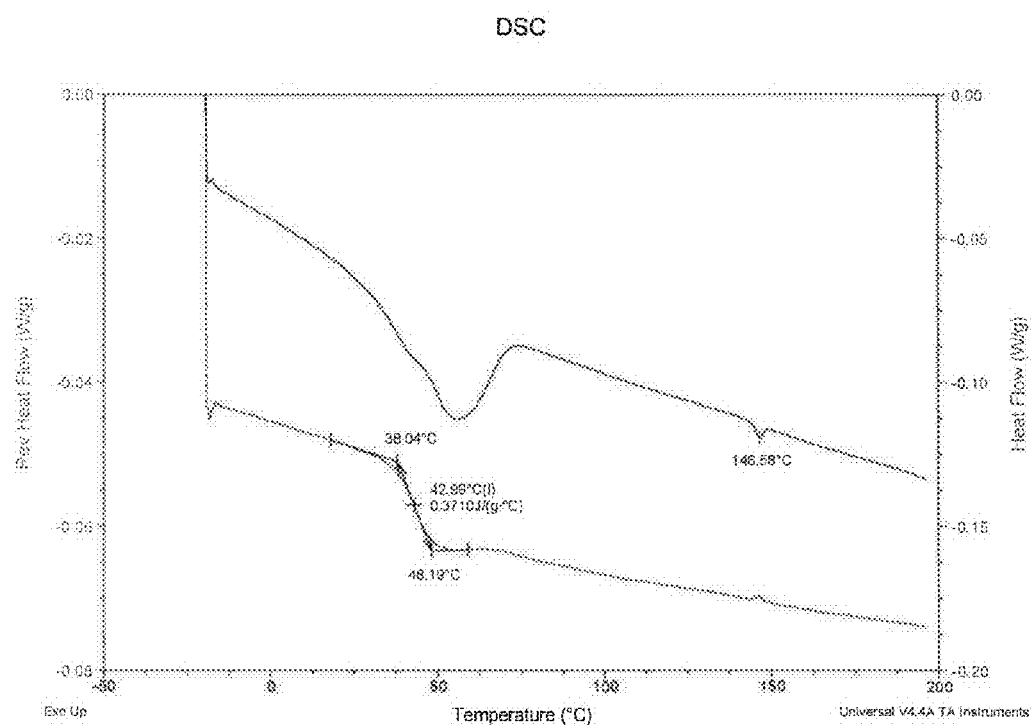
FIG. 8 depicts the modulated DSC thermogram of a 90/10 (w/w) amorphous paroxetine mesylate/PVP-VA solid dispersion, Example 2-4, prepared by spray drying.

XRPD pattern for 90/10 (w/w) paroxetine mesylate/PVP-VA, Example 2-4, shows the solid dispersion to be x-ray amorphous (FIG. 7). By mDSC, a single apparent $T_g$ is observed for this sample at approximately 43° C. (FIG. 8), which is slightly less than the $T_g$ of amorphous paroxetine mesylate (44° C.). A small endotherm is observed at approximately 147° C. in the total heat flow signal of mDSC (FIG. 8), which is likely due to melting of crystalline paroxetine mesylate Form A upon heating.

Figure 9:
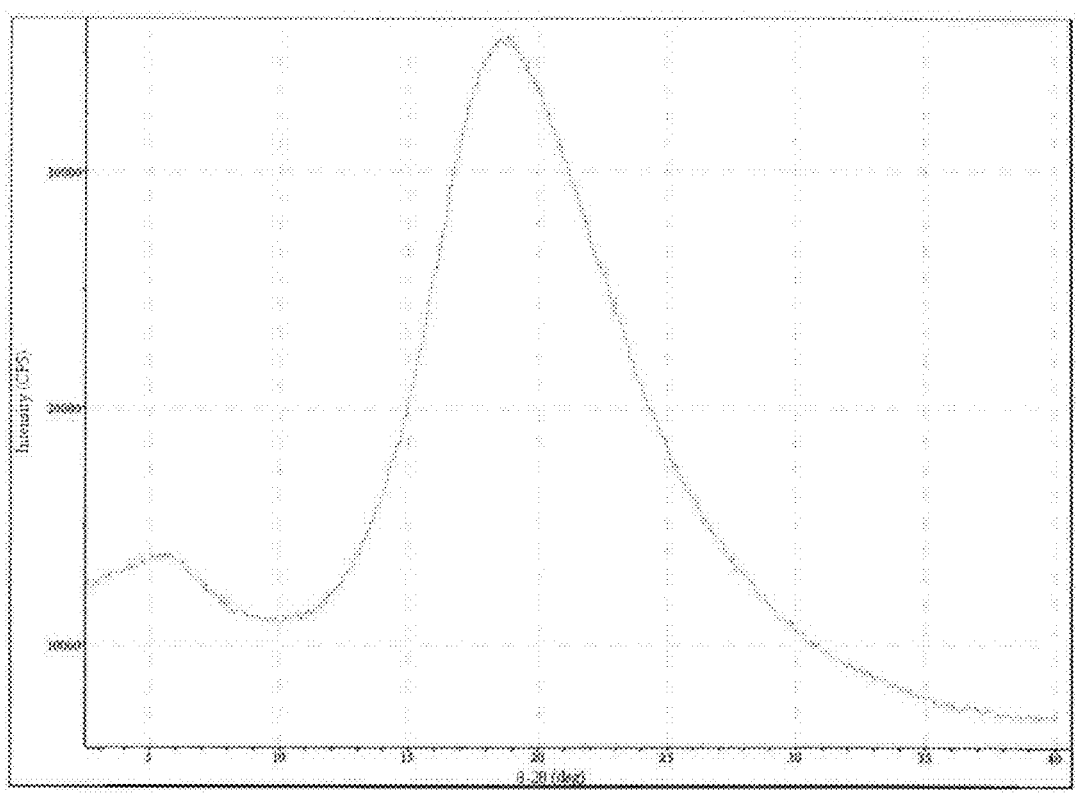
FIG. 9 depicts the XRPD pattern of a 90/10 (w/w) amorphous paroxetine mesylate/Eudragit L100 solid dispersion, Example 2-5, prepared by spray drying.
Figure 10:
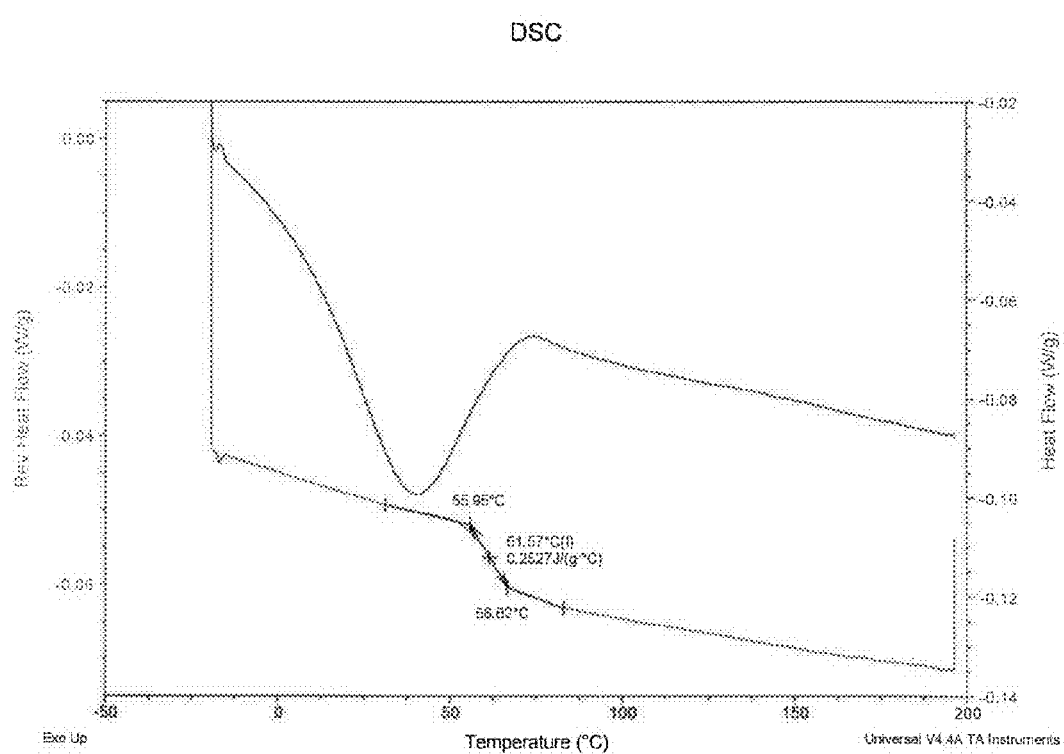
FIG. 10 depicts the modulated DSC thermogram of a 90/10 (w/w) amorphous paroxetine mesylate/Eudragit L100 solid dispersion, Example 2-5, prepared by spray drying.

XRPD pattern for 90/10 (w/w) paroxetine mesylate/Eudragit L100, Example 2-5, shows the solid dispersion to be x-ray amorphous (FIG. 9). By mDSC, a single apparent $T_g$ is observed for this sample at approximately 62° C. (FIG. 10), which is greater than the $T_g$ of amorphous paroxetine mesylate (44° C.).

Physical Stability of Spray Dried Dispersions

Physical stability experiments were conducted by exposing the dispersions in open containers at Room Temperature (RT) and at elevated temperature and different humidities (expressed as relative humidity, RH). Given the high aqueous solubility of paroxetine mesylate Form A (water: >1000 mg/mL), stress experiments by immersing the test samples in aqueous media were determined to be inappropriate, since paroxetine mesylate concentration in the test solution would likely not lead to crystallization of Form A and/or any crystalline Form A generated would likely rapidly dissolve making the assessment of physical instability (e.g., crystallization) difficult to judge. As the polymers used in this study are non-crystalline; observations of crystalline material are assumed to be the paroxetine mesylate crystalline phase and most likely paroxetine mesylate Form A. The physical stability was studied at RT/75% RH, at RT/58% RH, and at 60° C./75% RH. The results are discussed below and summarized in Table 3.

Physical stability was evaluated visually at RT/75% RH after approximately 24 h by PLM for evidence of birefringence and extinction indicative of crystalline material. Observations of birefringence/extinction along the edge of the material are likely due to strain effects or from edge refraction/reflection from the glassy flakes rather than a crystalline phase unless otherwise stated.

Upon exposure to RT/75% RH up to 24 h, deliquescence and birefringent particles with extinction consistent with a crystalline phase were observed for 90/10 (w/w) PM/PVP-VA, Example 2-4. Deliquescence was also observed for 90/10 (w/w) PM/Eudragit L100, Example 2-5, with birefringence/extinction observed along the edge of the test materials.

Upon exposure to RT/58% RH up to 3 days, no evidence of crystalline material was observed for 30/70 (w/w) PM/Eudragit L100, Example 2-1, and 70/30 (w/w) PM/Eudragit L100, Example 2-3. Deliquescence and birefringent particles with extinction consistent with a crystalline phase were observed for 90/10 (w/w) PM/PVP-VA. Deliquescence was also observed for 90/10 (w/w) PM/Eudragit L100, Example 2-5, with birefringence/extinction observed along the edge of the test materials. Deliquescence was observed for 50/50 (w/w) PM/PVP-VA, Example 2-2, solid dispersion.

Upon exposure to RT/58% RH up to 11 days, no evidence of crystalline material was observed for 30/70 (w/w) PM/Eudragit L100, Example 2-1, and 70/30 (w/w) PM/Eudragit L100, Example 2-3.

Upon exposure to 60° C/75% RH up to 2 h, deliquescence and birefringent particles with extinction consistent with a crystalline material were observed for, 90/10 (w/w) PM/PVP-VA, Example 2-4. Deliquescence was observed for 50/50 (w/w) PM/PVP-VA, Example 2-2; 70/30 (w/w) PM/Eudragit L100, Example 2-3; and 90/10 (w/w) PM/Eudragit L100, Example 2-5; with birefringence/extinction observed along the edge of the test materials.

Upon exposure to 60° C./75% RH up to 20 h, up to 48 h, up to 6 days and up to 14 days, no evidence of crystalline material was observed for any of 30/70 (w/w) PM/Eudragit L100, Example 2-1; 70/30 (w/w) PM/Eudragit L100, Example 2-3; 50/50 (w/w) PM/PVP-VA, Example 2-2; and 30/70 (w/w) PM/PVP-VA, Example 2-4.

(44° C.). This observation suggests a small, yet unexpected anti-plasticization effect. The $T_g$s for the stressed samples are similar to the $T_g$ for the as prepared material.

70/30 (w/w) PM/Eudragit L100 Solid Dispersion, Example 2-3

No evidence of crystalline material was observed for 70/30 (w/w) PM/Eudragit L100 solid dispersion upon exposure to RT/58% RH and 60° C./75% RH up to 4 weeks; however, deliquescence was observed and white solids changed to sticky substance upon exposure to 60° C./75% RH. No further characterization was performed. XRPD patterns for 70/30 (w/w) PM/Eudragit L100 as prepared and stressed showed that the stressed samples remained x-ray amorphous. By SEM, the particles as prepared are spheres with some wrinkles on the surface and a broad distribution of sizes with some agglomerates; the spheres are fused into large agglomerates for RT/58% RH stressed samples compared to the morphology for the as prepared material, which is likely due to moisture absorption during stress. Modulated DSC thermograms for 70/30 (w/w) PM/Eudragit L100 as prepared and stressed at RT/58% RH each displayed a single apparent $T_g$.

TABLE 3

Summary Table of Paroxetine Mesylate Solid Dispersion Screening

| | | | | Acceptable Physical Stability?[a] | | | | | | | |
|---|---|---|---|---|---|---|---|---|---|---|---|
| | | Characterization | | | RT/ 58% RH | RT/ 75% RH | 60° C./75% RH | | | | |
| Polymer | PM/polymer (w/w) & Example process | x-ray amorph | Single $T_g$ | $T_g$ (° C.) | 3 d | 11 d | 24 h | 2 h | 20 h | 48 h | 6 d | 14 d |
| — | 1-2 100/0 (FD)[b] | Y | Y | 44 | N | — | — | N | — | — | — | — |
| Eudragit L100 | 2-5 90/10 (SD) | Y | Y | 62 | Y[e] | — | Y[e] | Y[e] | — | — | — | — |
| | 1-3 70/30 (SD)[b,c] | Y | Y | 92 | Y | Y | — | Y[f] | Y[f] | Y[f] | Y[f] | Y[f] |
| | 2-3 70/30 (SD) | Y | Y | 91 | Y | Y | — | Y[e] | Y[e] | Y[e] | Y[e] | Y[e] |
| | 2-1 30/70 (SD) | Y | Y | 155 | Y | Y | — | Y | Y | Y | Y | Y |
| PVP-VA | 2-4 90/10 (SD) | Y | Y[d] | 43 | N | — | N | N | — | — | — | — |
| | 1-5 70/30 (FD)[b,c] | Y | Y | 60 | N | — | — | Y[f] | — | — | — | — |
| | 1-6 50/50 (FD)[b,c] | Y | Y | 84 | Y[f] | Y[f] | — | Y[f] | Y[f] | Y[f] | Y[f] | Y[f] |
| | 2-2 50/50 (SD) | Y | Y | 82 | Y[f] | Y[f] | — | Y[e] | Y[e] | Y[e] | Y[e] | Y[e] |
| | 1-7 30/70 (FD)[b,c] | Y | Y | 95 | Y[f] | — | — | Y[f] | Y[f] | Y[f] | Y[f] | Y[f] |

Y: yes; N: no; —: no data; FD: freeze drying; SD: spray drying
[a]physical stability is judged after elevated temperature and humidity stress. An answer of 'yes' indicates acceptable physical stability with no evidence of crystalline material.
[b]25° C./58% RH stress condition was used in this study instead of RT/58% RH.
[c]glass was observed after stress, which was assumed to be evidence that deliquescence occurred.
[d]$T_g$ similar to amorphous paroxetine mesylate (44° C.).
[e]some birefringence/extinctions were observed along the edge of material, which is likely due to strain effects or from edge refraction/reflection from the glassy flakes rather than a crystalline phase; however, deliquescence was observed after stress.
[f]no evidence of birefringence was observed; however, material deliquesced to sticky substance or glass after stress.

Discussion of Individual Spray Dried Dispersions

30/70 (w/w) PM/Eudragit L100 Solid Dispersion, Example 2-1

No evidence of crystalline material was observed for 30/70 (w/w) PM/Eudragit L100 solid dispersion upon exposure to RT/58% RH and 60° C./75% RH up to 4 weeks. XRPD patterns for 30/70 (w/w) PM/Eudragit L100 as prepared and stressed showed that the stressed samples remained x-ray amorphous. By SEM, the particles as prepared were collapsed spheres with a generally smooth surface and a broad distribution of sizes with some agglomerates; the morphology and surface appearance of the stressed samples remain similar to that of the as prepared material. Modulated DSC thermograms for 30/70 (w/w) PM/Eudragit L100 as prepared and stressed each displayed a single apparent $T_g$. The as prepared material displays a single apparent $T_g$ at approximately 155° C., which is greater than the $T_g$s for Eudragit L100 (150° C.) from its product literature and amorphous PM The $T_g$s determined for the stressed samples are similar to the $T_g$ for the as prepared material.

50/50 (w/w) PM/PVP-VA Solid Dispersion, Example 2-2

Figure 4:
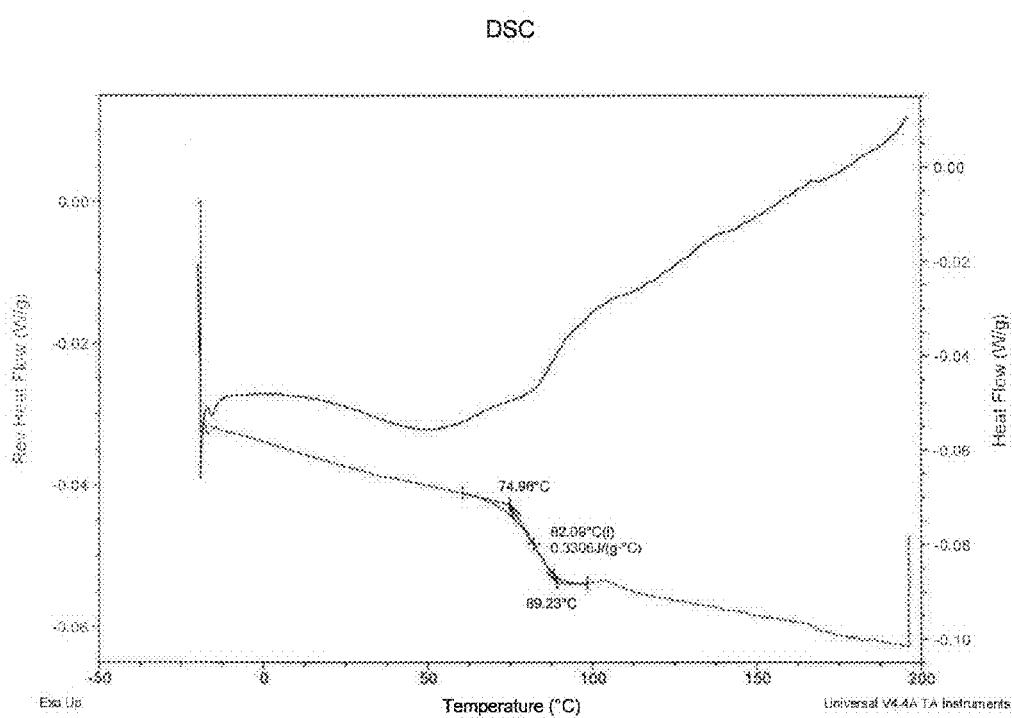
FIG. 4 depicts the modulated DSC thermogram of a 50/50 (w/w) amorphous paroxetine mesylate/PVP-VA solid dispersion, Example 2-2, prepared by spray drying.

By SEM, the particles as prepared are spheres with a generally smooth surface and a broader distribution of sizes with some agglomerates. By mDSC, a single apparent $T_g$ is observed at approximately 82° C. (FIG. 4). Deliquescence was observed for 50/50 (w/w) PM/PVP-VA and white solids changed to sticky substance upon exposure to RT/58% RH. No evidence of birefringence was observed by PLM. No further characterization was performed. Deliquescence was observed for 50/50 (w/w) PM/PVP-VA and white solids changed to light-brown, sticky substance upon exposure to 60° C./75% RH. XRPD patterns for 50/50 (w/w) PM/PVP-VA as prepared and stressed at 60° C./75% RH showed the stressed samples remain x-ray amorphous.

Example 4

Preparation and Characterization of Prototype Capsules

Figure 11:
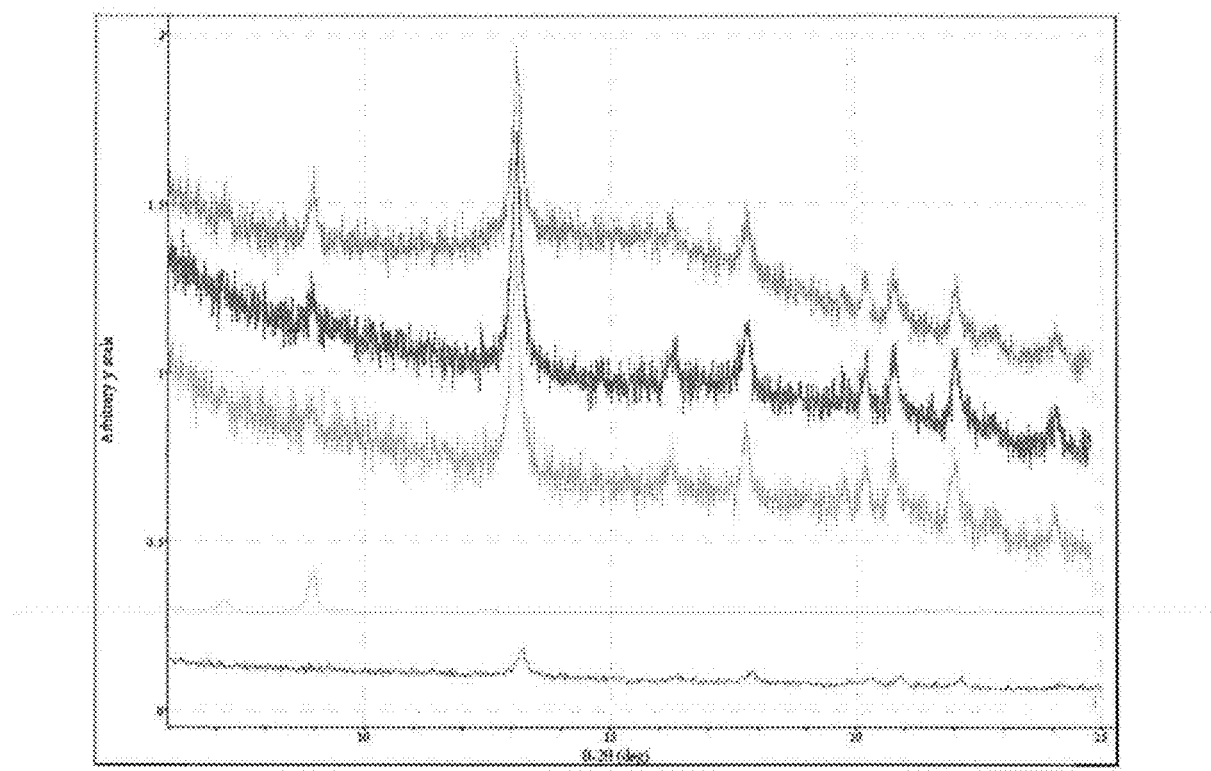
FIG. 11 is an overlay of XRPD patterns for prototype capsules containing amorphous paroxetine mesylate solid dispersions of the invention as prepared in Example 4.

The solid dispersions from Examples 2-1, 2-2 and 2-3 were blended with excipients to prepare 7.5 mg paroxetine mesylate capsules (Table 4A) to prepare prototype capsules. Table 4B presents additional batch formulations for paroxetine mesylate capsules. The prototype capsules from Table 4A were characterized as prepared by XRPD and Karl-Fischer titration (KF) for water content. The data and results are summarized in Table 5. An overlay of XRPD patterns for prototype capsules as prepared is shown in FIG. 11. The peak-to-noise ratio is very low in the range of 6-24.8°2θ for these patterns. By KF analysis, the prototype capsules containing 30/70, 70/30 (w/w) PM/Eudragit L100 and 50/50 (w/w) PM/PVP-VA contain similar water content—approximately 0.73, 0.75, and 0.75 wt % water, respectively.

TABLE 4

Formulation Information for 7.5 mg Paroxetine Mesylate Capsules
Batch Formula for Paroxetine (as Mesylate) Capsules, 7.5 mg

| Component | Pure PM % w/w | Pure PM mg/capsule | PM/PVP-VA (50/50) % w/w | PM/PVP-VA (50/50) mg/capsule | PM/Eudragit L100 (70/30) % w/w | PM/Eudragit L100 (70/30) mg/capsule | PM/Eudragit L100 (30/70) % w/w | PM/Eudragit L100 (30/70) mg/capsule |
|---|---|---|---|---|---|---|---|---|
| PM | 4.53 | 9.69 | 4.53 | 9.69 | 4.53 | 9.69 | 4.53 | 9.69 |
| Polymer | — | — | 4.53 | 9.69 | 1.94 | 4.15 | 10.57 | 22.61 |
| Dibasic Calcium Phosphate Anhydrous, unmilled | 91.84 | 196.54 | 87.31 | 186.85 | 89.90 | 192.39 | 81.28 | 173.93 |
| Sodium Starch Glycolate | 1.67 | 3.57 | 1.67 | 3.57 | 1.67 | 3.57 | 1.67 | 3.57 |
| Magnesium Stearate | 1.96 | 4.2 | 1.96 | 4.2 | 1.96 | 4.2 | 1.96 | 4.2 |
| Total | 100.00 | 214.00 | 100.00 | 214.00 | 100.00 | 214.00 | 100.01 | 214.00 |

TABLE 4B

Additional Batch Formulations for Paroxetine Mesylate (PM) Capsules

| Component | Potency 5 mg % W/W | 5 mg mg/capsule | 19.5 mg % W/W | 19.5 mg mg/capsule |
|---|---|---|---|---|
| 30:70 PM/Eudragit Solid dispersion | 10.06 | 21.53 | 39.24 | 83.98 |
| Dibasic Calcium Phosphate, Anhydrous | 86.31 | 184.7 | 57.17 | 122.25 |
| Sodium Starch Glycolate | 1.67 | 3.57 | 1.67 | 3.57 |
| Magnesium Stearate | 1.96 | 4.2 | 1.96 | 4.2 |
| Total | 100 | 214 | 100 | 214 |

TABLE 5

Characterization of Prototype Capsules (Table 4A) Containing Paroxetine Mesylate Solid Dispersions

| Dispersion (wt % PM/polymer) | Analysis | Result |
|---|---|---|
| (30/70) Eudragit L100 | visual observation | white powders |
|  | XRPD | no evidence of Form A |
|  | KF | 0.73 wt % water |
| (70/30) Eudragit L100 | visual observation | white powders |
|  | XRPD | no evidence of Form A |
|  | KF | 0.75 wt % water |
| (50/50) PVP-VA | visual observation | white powders |
|  | XRPD | no evidence of Form A |
|  | KF | 0.75 wt % water |
| magnesium stearate | XRPD | reference pattern |
| dibasic calcium phosphate | XRPD | reference pattern |

Physical Stability of Prototype Capsules

Physical stability of the prototype capsules containing solid dispersions of the invention was evaluated at RT/58% RH and 60° C./75% RH at 2 and 4 weeks. Materials were observed visually at each time point and characterized by XRPD. KF analysis was conducted for the capsules after storage up to 4 weeks for water content. The data were compared to the results for the as prepared materials. For all the capsules upon exposure to the examined stress conditions, no evidence of crystalline Form A was observed by XRPD analysis.

Prototype Capsules Containing a 30/70 (w/w) PM/Eudragit L100 Solid Dispersion, Example 2-1

An overlay of XRPD patterns for prototype capsules containing a 30/70 (w/w) PM/Eudragit L100 solid dispersion of the invention as prepared and stressed at RT/58% RH and 60°

Figure 12:
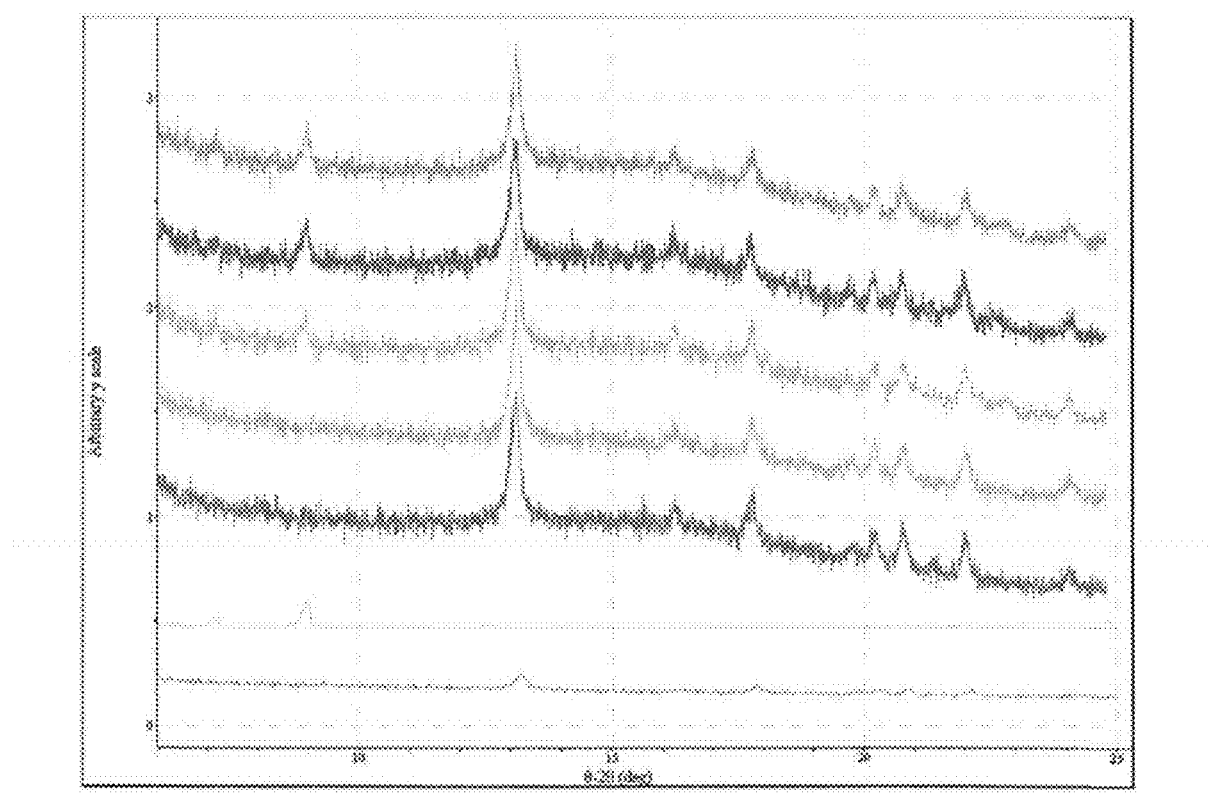
FIG. 12 is an overlay of XRPD patterns for prototype capsules containing a 30/70 (w/w) amorphous paroxetine mesylate/Eudragit L100 solid dispersion, Example 2-1, as prepared and stressed at RT/58% RH and 60° C./75% RH.

C./75% RH is shown in FIG. 12. By visual inspection, no apparent change was observed for the capsules upon exposure to RT/58% RH up to 4 weeks. At 60° C./75% RH after 4 weeks, the XRPD peak at approximately 8.9°2θ attributed to magnesium stearate is not visible, which is likely due to the deliquescence of magnesium stearate at a high relative humidity.

By KF analysis, the prototype capsules after storage at RT/58% RH and 60° C./75% RH for 4 weeks contain approximately 1.10 and 1.79 wt % water, respectively, which is greater than the water measured (0.73 wt %) for the as prepared capsule, Table 5.

Prototype Capsules Containing a 70/30 (w/w) PM/Eudragit L100 Solid Dispersion, Example 2-3

Figure 13:
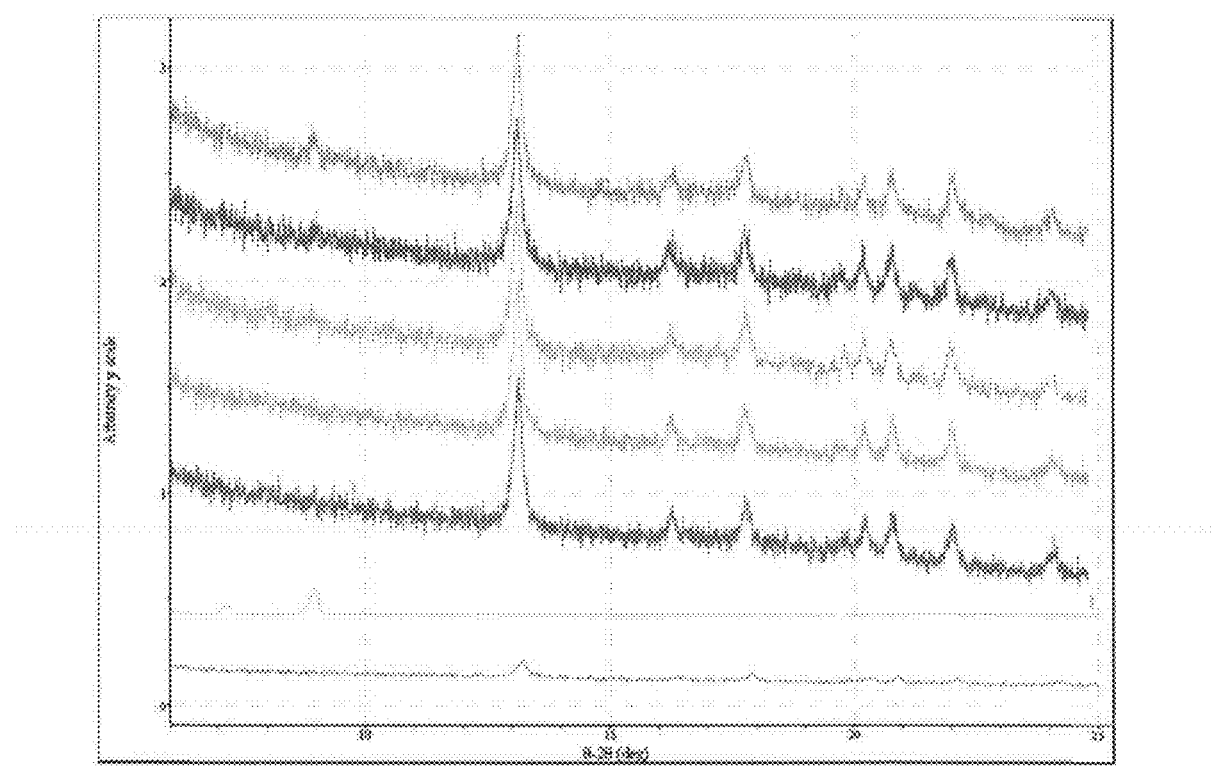
FIG. 13 is an overlay of XRPD patterns for prototype capsules containing a 70/30 (w/w) amorphous paroxetine mesylate/Eudragit L100 solid dispersion, Example 2-3, as prepared and stressed at RT/58% RH and 60° C./75% RH.

An overlay of XRPD patterns for prototype capsules containing a 70/30 (w/w) PM/Eudragit L100 solid dispersion of the invention as prepared and stressed at RT/58% RH and 60° C./75% RH is shown in FIG. 13. The observations are similar to those for prototype capsules containing 30/70 (w/w) PM/Eudragit L100, with the exception of some off-white agglomerates observed for the capsules containing 70/30 (w/w) PM/Eudragit L100 after storage at 60° C./75% RH.

By KF analysis, the prototype capsules after storage at RT/58% RH and 60° C./75% RH for 4 weeks contain relatively low water content values of approximately 0.82 and 0.61 wt % water, respectively.

Prototype Capsules Containing a 50/50 (w/w) PM/PVP-VA Solid Dispersion, Example 2-2

Figure 14:
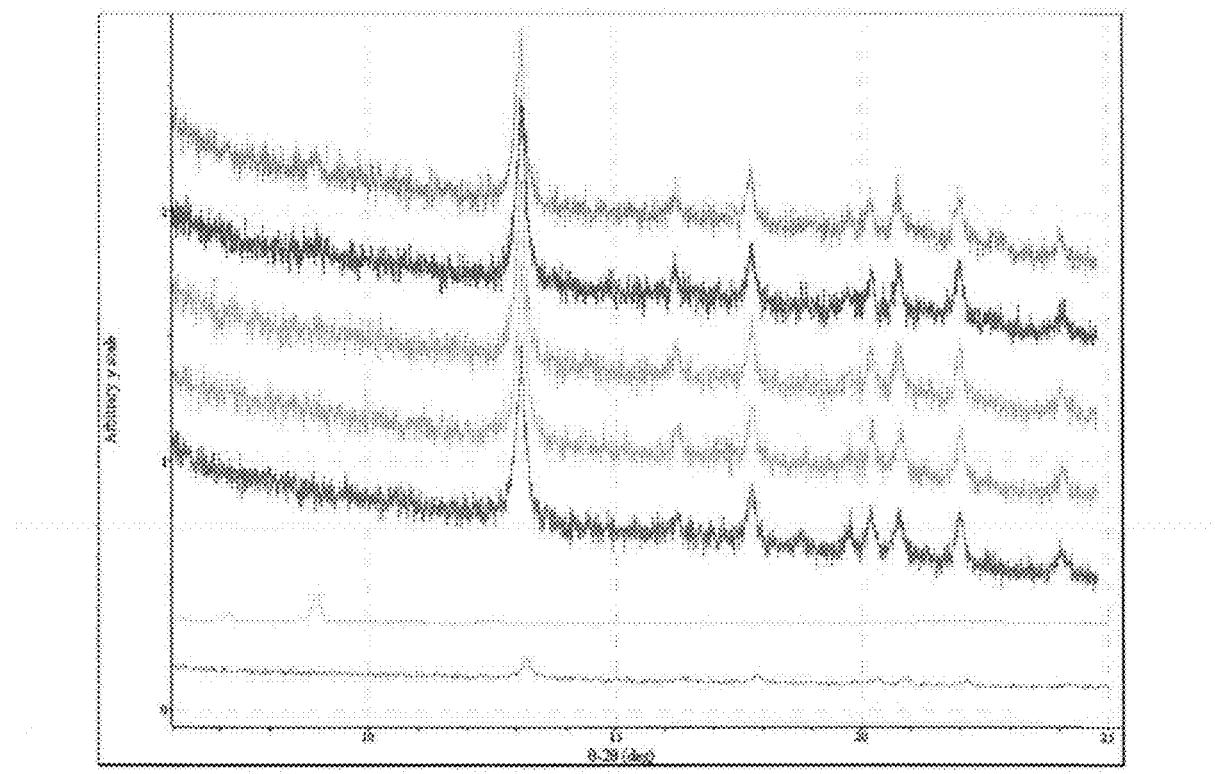
FIG. 14 is an overlay of XRPD patterns for prototype capsules containing a 50/50 (w/w) amorphous paroxetine mesylate/PVP-VA solid dispersion, Example 2-2, as prepared and stressed at RT/58% RH and 60° C./75% RH.

An overlay of XRPD patterns for prototype capsules containing a 50/50 (w/w) PM/PVP-VA solid dispersion of the invention as prepared and stressed at RT/58% RH and 60° C./75% RH is shown in FIG. 14. The observations are similar to those for prototype capsules containing a 30/70 (w/w) PM/Eudragit L100 solid dispersion of the invention, with the exception of some light-brown agglomerates observed for the capsules containing 50/50 (w/w) PM/PVP-VA after storage at 60° C./75% RH.

By KF analysis, the prototype capsules after storage at RT/58% RH and 60° C./75% RH for 4 weeks contain approximately 0.87 and 0.81 wt % water, respectively, which is greater than the water measured (0.75 wt %) for the as prepared capsule, Table 5.

Example 5

Solid State $^{19}$F NMR Studies

Solid-state $^{19}$F NMR spectra were acquired at ambient temperature using the method described above. A solid-sate $^{19}$F NMR spectra of a 30/70 (w/w) solid dispersion of paroxetine mesylate (PM) in Eudragit L100, (Example 2-1) is shown in FIG. 15. A comparison of the spectra of crystalline paroxetine mesylate Form A; lyophilized (amorphous) paroxetine mesylate (Example 1-2); the 30/70 (w/w) PM/Eudragit L100 solid dispersion (Example 2-1), and spray-dried Eudragit L100 (Example 1-4) is shown in FIG. 16. The $^{19}$F SSNMR spectrum of spray-dried Eudragit L100, having no fluorine atoms, showed no peaks. The spectrum of crystalline paroxetine mesylate Form A exhibits a relatively narrow $^{19}$F peak (51.8 ppm, peak width half height (PWHH): 965 Hz) that is indicative of crystalline material compared to the broad peaks observed in amorphous materials. The spectrum of lyophilized (amorphous) paroxetine mesylate has a slightly narrower $^{19}$F peak (50.9 ppm, PWHH: 2694 Hz) compared to the peak (51.3 ppm, PWHH: 3160 Hz) of the 30/70 (w/w) PM/Eudragit L100 solid dispersion. This suggests that the lyophilized (amorphous) paroxetine mesylate has more local order than the 30/70 (w/w) PM/Eudragit L100 solid dispersion. The peaks in the spectrum of the amorphous materials are shifted to lower frequency compared to crystalline paroxetine mesylate Form A.

The claimed invention is:

1. A solid dispersion of amorphous paroxetine mesylate in a copolymer of vinylpyrrolidone and vinylacetate, wherein the weight ratio of amorphous paroxetine mesylate to copolymer ranges from about 30:70 to about 50:50.

2. A solid dispersion of claim 1, wherein the weight ratio of paroxetine mesylate to polymer is selected from about 30:70 and about 50:50.

3. A solid dispersion of claim 1, having a single glass transition temperature.

4. A solid dispersion of claim 1 being stable for at least 48 hours at 60° C. and 75% relative humidity.

5. A pharmaceutical composition of paroxetine mesylate comprising the solid dispersion of claim 1 and at least one pharmaceutically acceptable excipient, wherein the paroxetine mesylate is present in a therapeutically acceptable amount.

6. A pharmaceutical composition of claim 5 wherein the pharmaceutically acceptable excipient comprises anhydrous dibasic calcium phosphate, sodium starch glycolate and magnesium stearate, wherein the sodium starch glycolate is present in an amount of up to about 2 percent by weight of the pharmaceutical composition and the magnesium stearate is present in an amount of up to about 2 percent by weight of the pharmaceutical composition.

* * * * *